United States Patent [19]

Kabat

[11] Patent Number: 5,794,807
[45] Date of Patent: Aug. 18, 1998

[54] PROTECTIVE COVER FOR EVIDENCE

[76] Inventor: Thomas W. Kabat, 4165 Manke Rd., Fairgrove, Mich. 48733

[21] Appl. No.: 819,678

[22] Filed: Mar. 17, 1997

[51] Int. Cl.$^6$ .................................................. B65D 45/00
[52] U.S. Cl. ......................... 220/315; 220/359; 220/377; 220/380; 220/DIG. 13; 47/29
[58] Field of Search ..................... 220/200, 315, 220/359, 377, 380, 4.25, DIG. 13; 47/9, 29

[56] References Cited

U.S. PATENT DOCUMENTS

| | | |
|---|---|---|
| 1,930,939 | 10/1933 | Horner . |
| 2,004,449 | 6/1935 | Stanley . |
| 2,226,841 | 12/1940 | Barnhart . |
| 2,814,381 | 11/1957 | Stevik ............................ 220/377 X |
| 3,093,930 | 6/1963 | Witkowski . |
| 3,214,865 | 11/1965 | Rosenvold et al. . |
| 3,384,992 | 5/1968 | Heffron . |
| 3,620,411 | 11/1971 | Rump ............................ 220/377 X |
| 3,652,142 | 3/1972 | Kreutzweiser ................. 220/377 X |
| 4,013,214 | 3/1977 | Hansen et al. ................. 220/377 X |
| 4,422,560 | 12/1983 | Solomon ........................ 220/377 |
| 4,682,701 | 7/1987 | Katz .............................. 215/230 |
| 4,919,426 | 4/1990 | Vieira . |
| 5,055,215 | 10/1991 | Maine et al. .................. 220/359 X |

*Primary Examiner*—Stephen Cronin
*Attorney, Agent, or Firm*—Reising, Ethington, Learman & McCulloch, PLLC

[57] ABSTRACT

A protective cover adapted to be placed over an article of physical evidence or other object has a dome-shaped body open at one end encircled by a peripheral flange. The flange is provided with retainers operable to restrain inadvertent movement of the cover once it has been placed on a substrate in overlying relation to the object.

12 Claims, 1 Drawing Sheet

U.S. Patent    Aug. 18, 1998    5,794,807
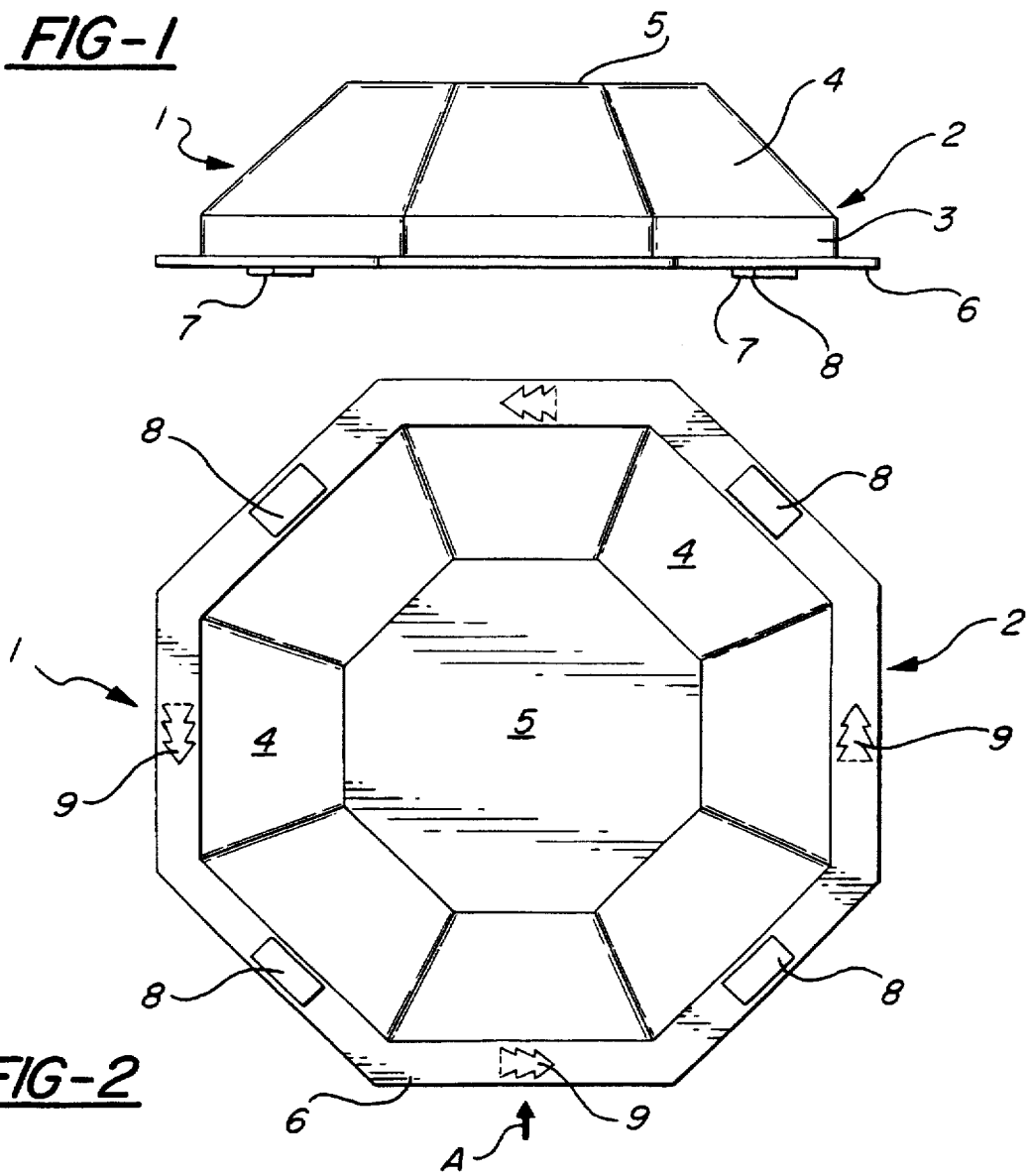
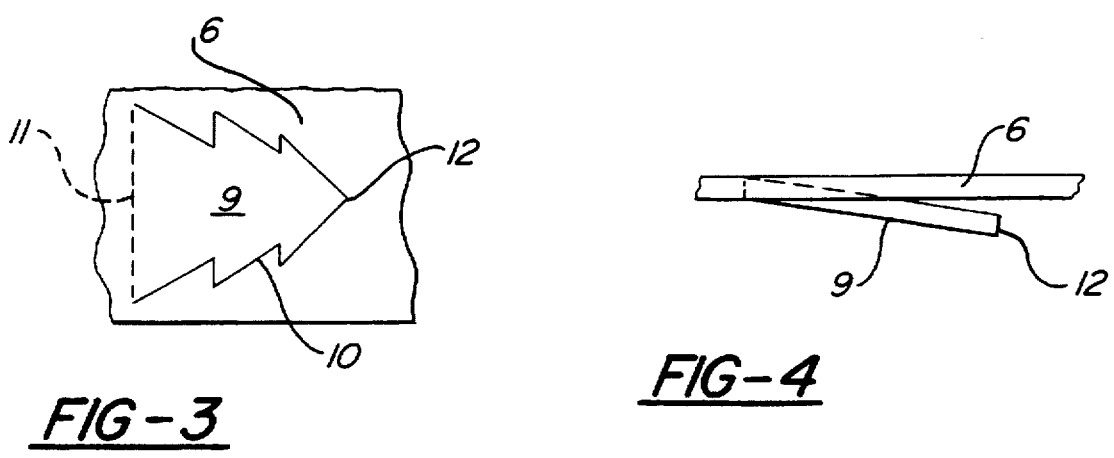

PROTECTIVE COVER FOR EVIDENCE

This invention relates to a protective cover that is adapted to be placed on a substrate so as to overlie and protect physical evidence.

BACKGROUND OF THE INVENTION

One of the major problems encountered by investigators at crime and accident scenes is the protection of articles of physical evidence against contamination or movement. It is common practice for investigating officials to enclose an investigation area by means of ropes or tapes, but little attention appears to have been given to protecting articles against movement, removal, or contamination by humans, animals, and the elements. For example, an article of evidence such as a glove lying on the ground at a crime scene may be moved by a person, a dog, or a squirrel. It also may be moved by a gust of wind and saturated by rain or snow. In such instances the article of evidence may not be as useful as it would have been had it not been moved or contaminated.

An object of this invention is to provide a protective cover which may be positioned over an article of physical evidence to protect the latter against inadvertent movement or contamination.

SUMMARY OF THE INVENTION

A protective cover constructed in accordance with the invention comprises an upright, dome-shaped hollow body closed at its upper end and open at its lower end. A peripheral flange encircles the lower end of the body and extends laterally outwardly therefrom. The flange carries on its lower surface adhesive retaining means which enables the cover to be secured to a substrate such as a brick or concrete sidewalk. The flange also includes fingers which normally lie in the plane of the flange, but which may be deformed out of such plane so as to project below the plane for engagement with grass or other vegetation. In either case the cover will overlie the article of evidence and be restrained against inadvertent dislodgment. The presence of the cover also will serve to inform investigators of the location of an article.

THE DRAWINGS

A protective cover constructed in accordance with the preferred embodiment of the invention is disclosed in the accompanying drawing wherein:

FIG. 1 is a side elevational view of the cover;

FIG. 2 is a bottom plan view;

FIG. 3 is a fragmentary, top plan view on an enlarged scale of a portion of the cover's flange; and FIG. 4 is a fragmentary elevational view of a portion of the flange as viewed in the direction of the arrow A in FIG. 2.

THE PREFERRED EMBODIMENT

A protective cover constructed in accordance with the presently preferred embodiment of the invention is designated generally by the reference character 1 and comprises an upstanding, hollow, dome-shaped body 2 having a plurality of upstanding side walls 3 joined at their upper ends to upwardly inclined panels 4 terminating in a flat top wall 5. In the preferred embodiment there are eight side walls 3 and eight panels 4. The panels 4 and the top wall 5 preferably are flat so as to enable labels or the like (not shown) to be applied to the top or one or more of the panels to identify an article underlying the cover and the person who placed the cover over such article.

The body 2 terminates at its lower end in a peripheral flange 6 which is flat on its upper and lower surfaces. At spaced intervals about its periphery the lower surface of the flange 6 is provided with adhesive retainers 7, each of which has an adhesive surface pressed against the lower surface of the flange 6 and each of which also has an outer adhesive surface which carries a peelable strip 8 which may be removed so as to expose the adhesive.

The flange 6 also is provided with a plurality of peripherally spaced retaining fingers 9 each of which is die-cut to form serrated edges 10. The flange 6 also is scored as at 11 to facilitate bending of each finger 9 downwardly out of the plane of the flange 6 so that the tip or free end 12 of the finger projects below the plane of the flange. This makes it possible for the tip of each finger to be embedded in grass or the like. As is shown clearly in FIG. 2, the free ends of all of the fingers 9 extend counterclockwise with respect to the periphery of the body 2.

The material from which the cover is made preferably is waterproof and transparent. Any one of a number of plastic materials is suitable. The panels 4 slope upwardly, thereby enabling a plurality of covers to be stacked in nested relation for transport or storage.

In the use of the cover, it may be placed over an object to be protected and stickers or labels bearing appropriate information applied to the top 5 or any of the sides 4. If the article that is to be protected lies upon a smooth substrate, such as a paved street or sidewalk, the strips 8 may be peeled from the retainers 7 so as to expose the adhesive and the flange pressed firmly against the substrate to enable the cover to resist inadvertent movement by wind gusts. If the article to be protected lies on a substrate such as grass, the fingers 9 may be deflected downwardly and out of the plane of the flange 6, following which the cover may be placed over the object to be protected and then rotated slightly counterclockwise (as viewed in FIG. 2) so as to embed the fingers in the grass. The serrated edges of the fingers will react with the grass blades to resist inadvertent movement of the cover.

The disclosed embodiment is representative of a presently preferred form of the invention, but is intended to be illustrative rather than definitive thereof. The invention is defined in the claims.

I claim:

1. A cover adapted to be placed upon a substrate in overlying relation thereto, said cover comprising an upright, dome-shaped, hollow body closed at its upper end and open at its lower end, a flange encircling said body and extending laterally of said body at said lower end, and retaining means carried by said flange engageable with said substrate and underlying said flange for removably coupling said body to said substrate, said retaining means comprising a finger forming part of and normally coplanar with said flange, said finger having one end deformable out of the plane of said flange to project below said flange.

2. The cover according to claim 1 wherein said retaining means comprises at least one strip secured to said flange and having an adhesive surface in a position to confront said substrate.

3. The cover according to claim 1 wherein said finger tapers toward said free end.

4. The cover according to claim 3 wherein said finger has serrated side edges.

5. The cover according to claim 1 wherein said body is formed of transparent material.

6. The cover according to claim 1 wherein said body has a flat top.

7. The cover according to claim 1 wherein said body has planar sides.

8. The cover according to claim 1 wherein said cover is octagonal.

9. A cover adapted to be placed upon a substrate in overlying relation thereto, said cover comprising an upright, dome-shaped, hollow body closed at its upper end and open at its lower end, a flange encircling said body and extending laterally of said body at said lower end, and retaining means carried by said flange engageable with said substrate for removably coupling said body to said substrate, said retaining means comprising a bendable finger forming part of and normally coplanar with said flange, said finger having one end deformable out of the plane of said flange to project below said flange, said finger when bent out of the plane of said flange permanently occupying a position inclined to the plane of said flange in the direction of said substrate.

10. A cover adapted to be placed upon a substrate in overlying relation thereto, said cover comprising an upright, crowned, hollow body closed at its upper end and open at its lower end, a planar flange secured to said body at said lower end and encircling said body, said flange projecting laterally and outwardly of said body and having a substantially flat lower surface adapted to seat upon said substrate, and a plurality of circumferentially spaced retaining means carried by said flange in positions when said cover is in use to confront and engage said substrate, said retaining means being cooperable with said substrate to restrain movement of said body relative to said substrate.

11. The cover according to claim 10 wherein each of said restraining means comprises an adhesive layer facing downwardly of said flange.

12. The cover according to claim 11 including a peelable strip overlying said adhesive layer and being removable therefrom to expose said adhesive layer to said substrate.

\* \* \* \* \*